(12) United States Patent
Anderson

(10) Patent No.: US 10,368,588 B2
(45) Date of Patent: Aug. 6, 2019

(54) UNDERGARMENT FOR MASKING SCOLIOSIS

(71) Applicant: Brenda Anderson, Caledonia, MI (US)

(72) Inventor: Brenda Anderson, Caledonia, MI (US)

(*) Notice: Subject to any disclaimer, the term of this patent is extended or adjusted under 35 U.S.C. 154(b) by 0 days.

(21) Appl. No.: 14/341,136

(22) Filed: Jul. 25, 2014

(65) Prior Publication Data

US 2015/0101618 A1 Apr. 16, 2015

Related U.S. Application Data

(60) Provisional application No. 61/961,339, filed on Oct. 11, 2013.

(51) Int. Cl.
| | | |
|---|---|---|
| *A41B 9/12* | (2006.01) | |
| *A61F 5/02* | (2006.01) | |

(52) U.S. Cl.
CPC ............. *A41B 9/12* (2013.01); *A61F 5/024* (2013.01); *A41B 2400/38* (2013.01)

(58) Field of Classification Search
CPC .. A61F 5/02; A61F 5/028; A61F 5/024; A61F 5/026; A63B 71/12; A63B 2071/1208; A41D 13/0153; A41D 13/0556; A41D 13/0562; A41B 9/12; A41B 2400/38
USPC ........................................................ 2/44, 45
See application file for complete search history.

(56) References Cited

U.S. PATENT DOCUMENTS

| | | | | |
|---|---|---|---|---|
| 1,924,016 A | * | 8/1933 | Barrows ........................ 602/19 |
| 2,632,178 A | * | 3/1953 | Kennedy ........................ 2/267 |
| 2,687,129 A | * | 8/1954 | Talkish .......................... 602/19 |
| 3,257,666 A | * | 6/1966 | Hoffman ............ A41D 13/0151 |
| | | | | 2/267 |
| 3,292,616 A | * | 12/1966 | Freeman ........................ 602/19 |
| 3,484,868 A | * | 12/1969 | Davenport, Jr. ....... A63B 71/12 |
| | | | | 2/23 |
| 3,871,367 A | * | 3/1975 | Miller ............................ 602/19 |
| 4,120,297 A | * | 10/1978 | Rabischong et al. .......... 602/19 |
| 4,202,327 A | * | 5/1980 | Glancy .......................... 602/19 |
| 4,272,848 A | * | 6/1981 | Hoofnagle ...................... 2/113 |
| 4,688,558 A | * | 8/1987 | Hooper et al. ................. 602/19 |
| 5,072,725 A | * | 12/1991 | Miller ............................ 602/19 |
| 5,074,288 A | * | 12/1991 | Miller ............................ 602/19 |
| 5,158,531 A | * | 10/1992 | Zamosky ....................... 602/19 |
| 5,256,135 A | * | 10/1993 | Avihod .......................... 602/19 |

(Continued)

*Primary Examiner* — Danny Worrell
(74) *Attorney, Agent, or Firm* — Gardner, Linn, Burkhart & Ondersma LLP

(57) ABSTRACT

An undergarment is provided for discretely altering the outward appearance of a person who has scoliosis or other physical deformity, in order to mask or obscure the deformity. The undergarment includes a main garment, a plurality of garment attachment elements spaced along inside surfaces of the main garment, a shoulder insert, and a torso insert. The shoulder insert has its own attachment element for releasable engagement with at least one of the garment attachment elements located in a shoulder portion of the main garment, and likewise the torso insert has its own attachment elements for releasable engagement with garment attachment elements located in a torso region of the main garment. The torso insert is configured to simultaneously extend along at least one of the garment's side portions (i.e., along a wearer's side) and the front and/or back portion of the garment.

19 Claims, 8 Drawing Sheets

(56) References Cited

U.S. PATENT DOCUMENTS

| | | | | |
|---|---|---|---|---|
| 5,555,562 | A * | 9/1996 | Holt et al. | 2/69 |
| 5,582,583 | A * | 12/1996 | Ballantyne | 602/5 |
| 5,599,286 | A * | 2/1997 | Labelle et al. | 602/19 |
| 5,718,670 | A * | 2/1998 | Bremer | 602/19 |
| 5,937,441 | A * | 8/1999 | Raines | 2/69 |
| 6,321,388 | B1 * | 11/2001 | Hildebrandt | 2/69 |
| 6,364,851 | B1 * | 4/2002 | Nafpliotis | 602/19 |
| 7,090,558 | B2 * | 8/2006 | Ott | 450/89 |
| 7,744,511 | B2 * | 6/2010 | Grigoriev et al. | 482/124 |
| 7,784,116 | B2 * | 8/2010 | Gallo | A41D 31/0044 2/267 |

* cited by examiner

UNDERGARMENT FOR MASKING SCOLIOSIS

RELATED APPLICATIONS

This invention is based on applicant's provisional application Ser. No. 61/961,339, filed on Oct. 11, 2013.

FIELD OF INVENTION

This invention relates to clothing that can be worn by those with scoliosis to reduce any visible deformity.

BACKGROUND OF THE INVENTION

The goal project are first to design masked methods for scoliosis spines. Scoliosis is a three-dimension deformity of the spinal column which occurs in girls mostly, and others during adolescence. The spine has three main sections, cervical, thoracic, and lumbar. There are seven cervical vertebrae (C1-C7) twelve thoracic (T1-T12), and five lumbar (L1-L5).

The present invention is an undergarment to help people with scoliosis, which is an abnormal curvature of the spine. The present invention is a stylish undergarment top worn under clothing to mask scoliosis (curvature), as well as helping people build confidence and self-esteem.

Having scoliosis can have a devastating social and emotional impact on lives. The present invention is a soft and comfortable spandex undergarment. The inside pockets attachment conceals, hides, and masks the scoliosis.

The present invention solves unmet need to provide scoliosis patients with, a comfortable, fashionable alternative to masked deformity of the spine while boosting self-esteem and lifestyle. The present invention is one of its kind undergarment top worn under clothing. It is designed as well to boost each scoliosis patient with confidence.

According to the National Scoliosis Foundation, there are approximately six (6) million people in the United States that are diagnosed with scoliosis. Each year, an estimated 30,000 children are fitted for brace and 100,000 children and adults will have surgery.

While spine surgery is an option, this invasive procedure presents a risk of complications, including a small risk of paralysis and sometimes a life full of pain.

With the physical effect of scoliosis, one also is vulnerable to feelings of self-conscious and isolated from their peers.

The present invention is unlike anything currently available on the market today. The undergarment of the present invention may come in one size fits all. It is stylish, soft and comfortable and made with a light weight breathable spandex.

Multiple embodiments of the system are disclosed herein. It will be understood that other objects and purposes of the invention, and variations thereof, will be apparent upon reading the following specification and inspecting the accompanying drawings.

SUMMARY OF INVENTION

Brief Description of the Drawings

For a fuller understanding of the invention, reference should be made to the following detailed description, taken in connection with the accompanying drawings, in which:
Brief description of drawings Specification.

DETAILED DESCRIPTION OF THE PREFERRED EMBODIMENT

Figure 1:
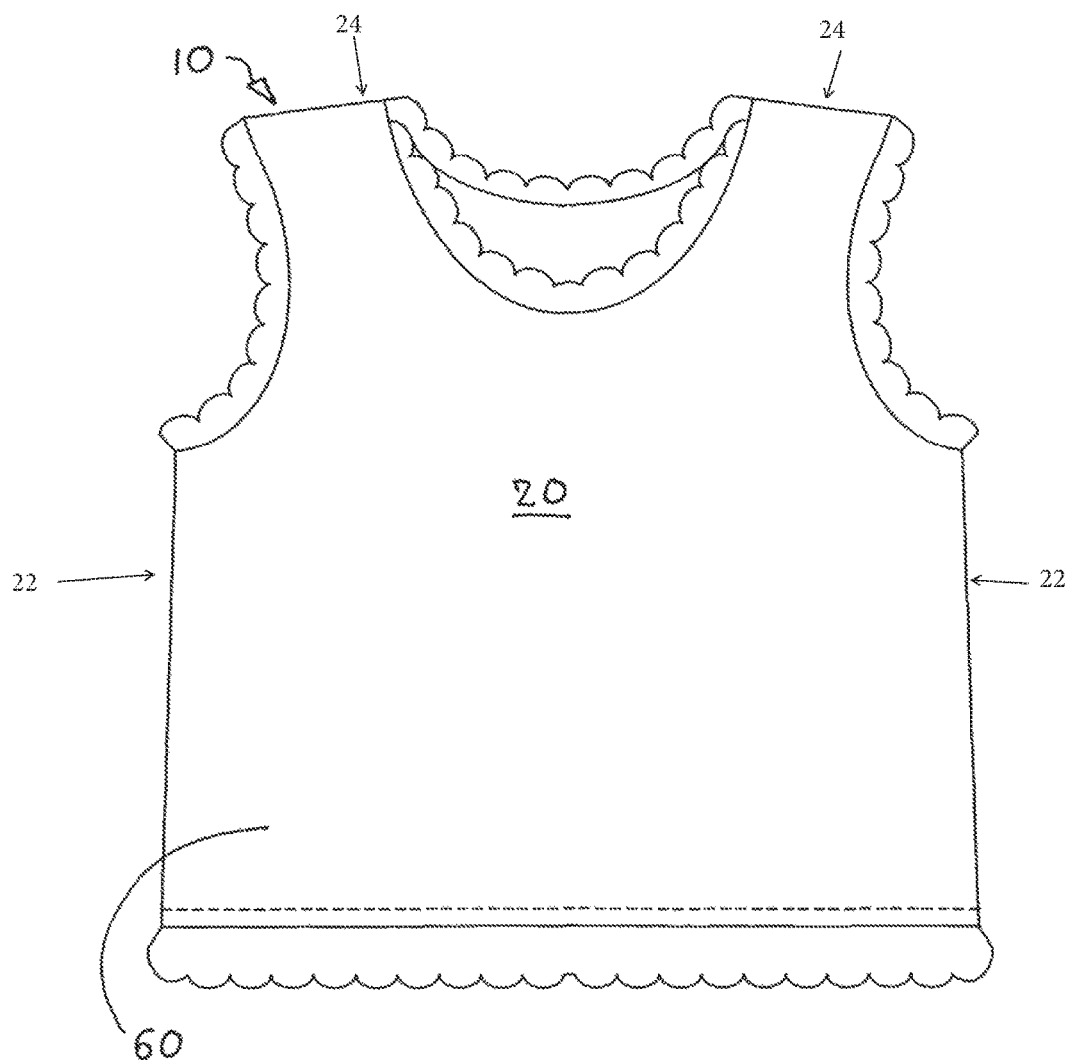
FIG. 1 is an embodiment of a pictorial of a front view of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

Certain terminology will be used in the following description for convenience and reference only, and will not be limiting. For example, the words "upwardly," "downwardly," "rightwardly," and "leftwardly" will refer to directions in the drawings to which reference is made. The words "inwardly" and "outwardly" will refer to directions toward and away from, respectively, the geometric center of the system and designated parts. Said terminology will include the words specifically mentioned, derivatives, and similar words. Also, "connected to," "secured to," or similar language includes the definitions "indirectly connected to," "directly connected to," "indirectly secured to," and "directly secured to."

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose.

In one embodiment of the present invention 10, it may have an adjustable shoulder insert 40, and an adjustable lower insert 50. When the adjustable shoulder insert 40 and/or an adjustable lower insert 50 are attached to the main garment 60 for easy application masking position of one lower shoulder caused by scoliosis.

The present invention 10 may also have a pocket embedded with a soft cushion like material and provide exceptional support. The cushion like material may be clothing, padding, or expandable by an air pump.

In one embodiment, this will be a one size fits all garment 10.

The present invention may change the appearance of the individual's curvature, to look as if they don't have any abnormalities in their spine and/or side or shoulder.

FIG. 1 illustrates a front view of an embodiment of the present invention 10, which may be referred to as an undergarment for scoliosis patients 10. FIG. 1 illustrates the main garment 60 having a front portion 20, opposite side portions 22, and opposite shoulder portions 24.

Figure 2:
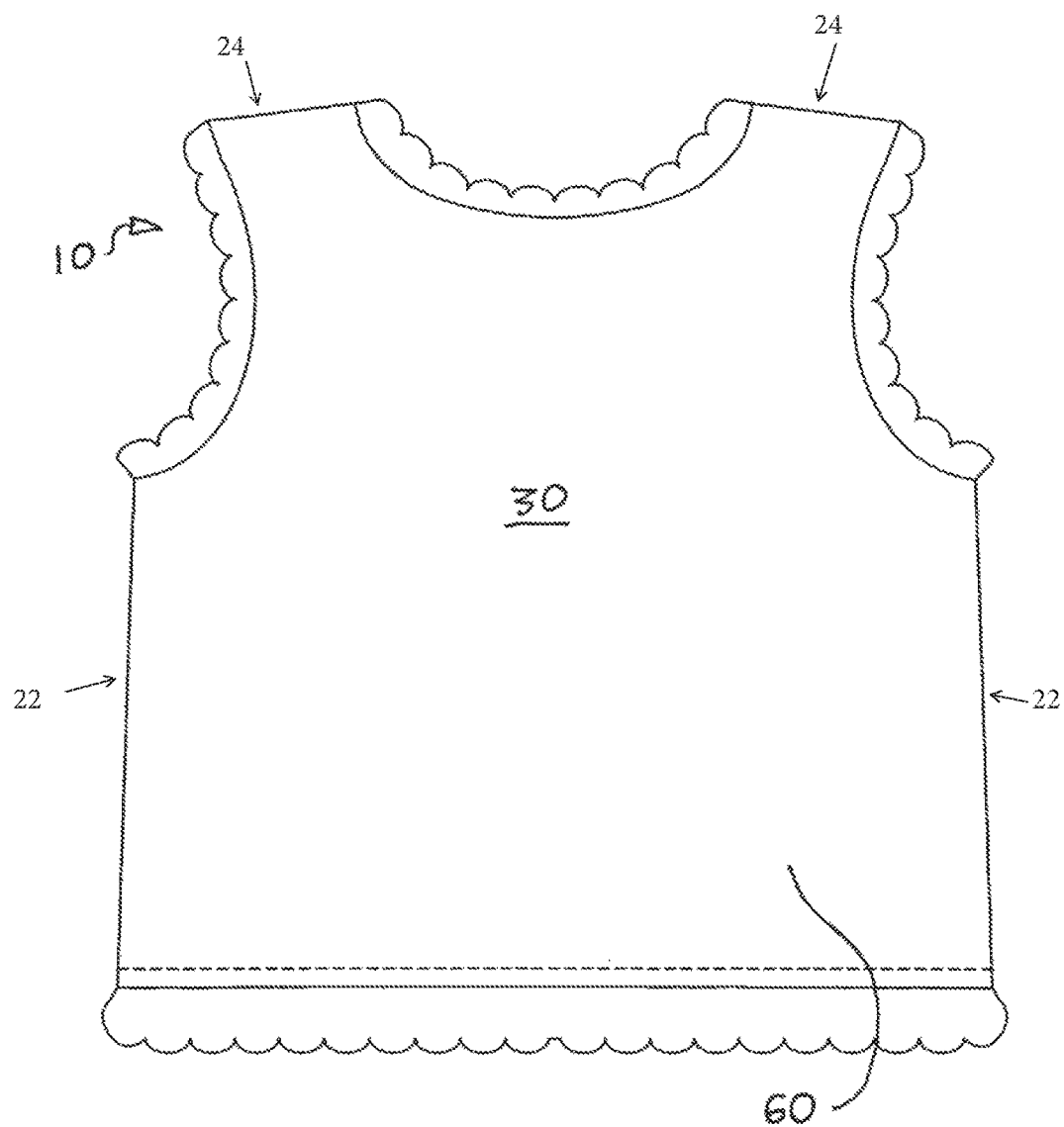
FIG. 2 is an embodiment of a pictorial of a back view.

FIG. 2 illustrates the main garment 60 having a rear or back portion 30, the opposite side portions 22, and opposite shoulder portions 24.

Figure 3:
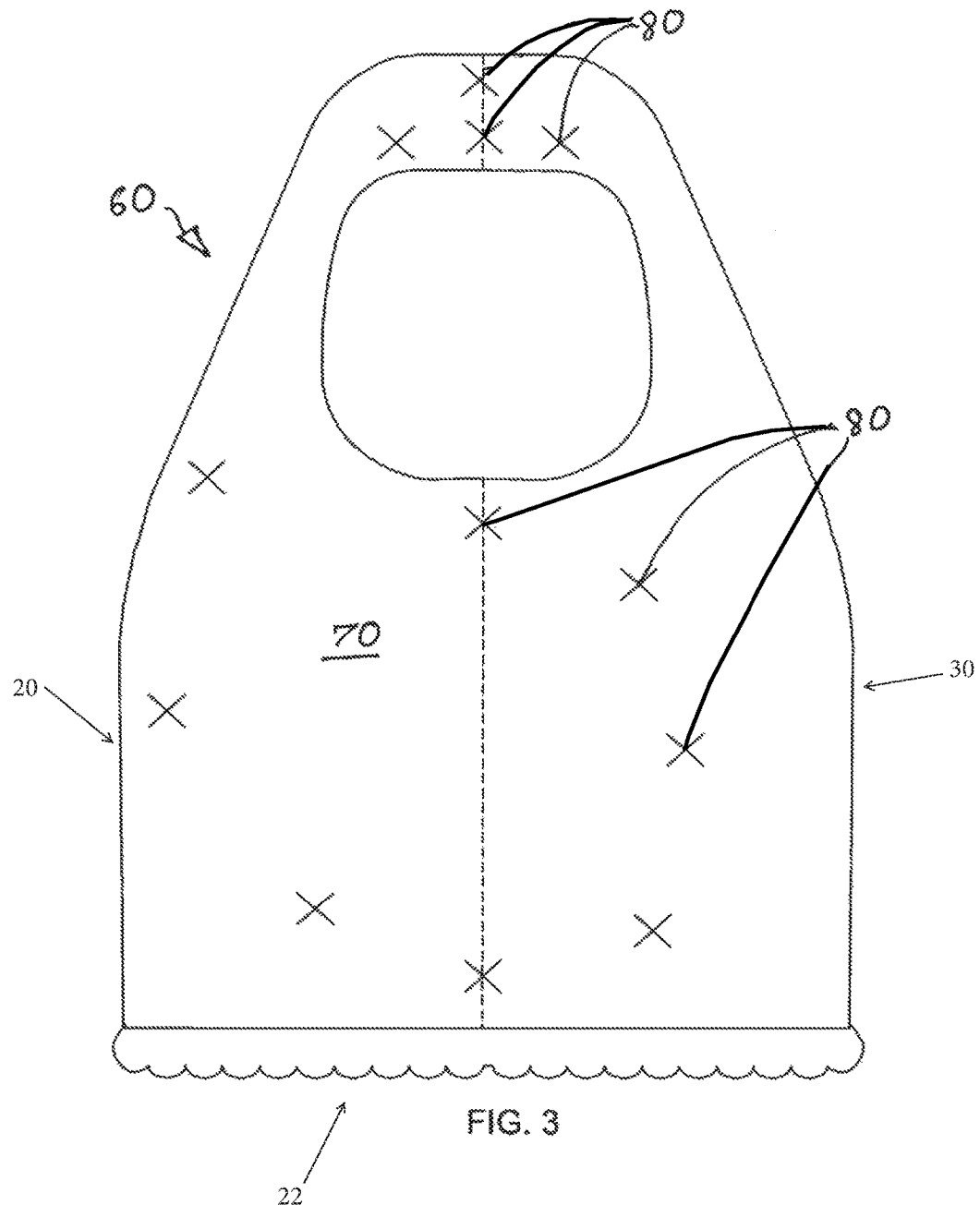
FIG. 3 is an embodiment of a pictorial of an inside view.

FIG. 3 illustrates the main garment 60 from one side 22 of the garment 60, the main garment 60 having an inside 70. An attachment means 80, or attachment elements 80, or means for attachment 80 are provided along the inside 70. A shoulder insert 40 or lower insert 50 may be removably attached to the attachment means 80. The attachment means 80 can be hook and loop such as Velcro®, snaps, or adhesive material. The attachment means 80 is to removably secure a shoulder insert 40, lower insert 50, or other similar item to the inside of the main garment 60. As illustrated in FIG. 3, the means for attachment 80 may be disposed in spaced arrangement on the inside 70 of the garment 60 and located anywhere the user desires on the inside 70 of the main garment 60.

Figure 4:
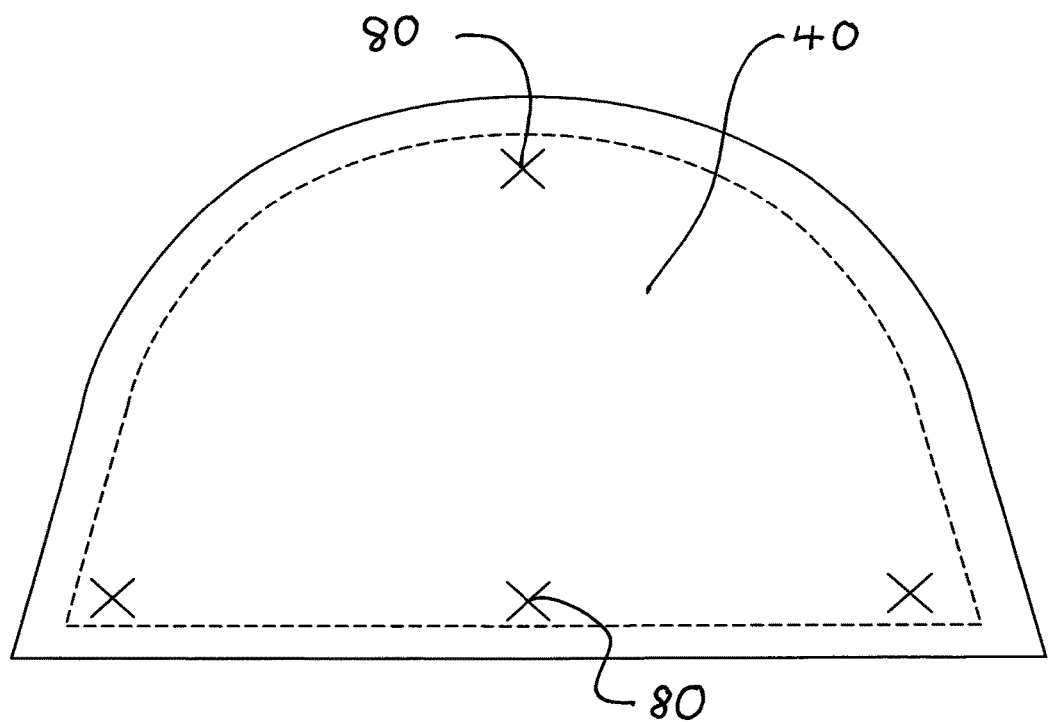
FIG. 4 is an embodiment of a shoulder insert.

FIG. 4 illustrates a shoulder insert 40 with its own attachment elements or attachment means 80 to removably attach to the attachment means 80 of the inside 70.

Figure 5:
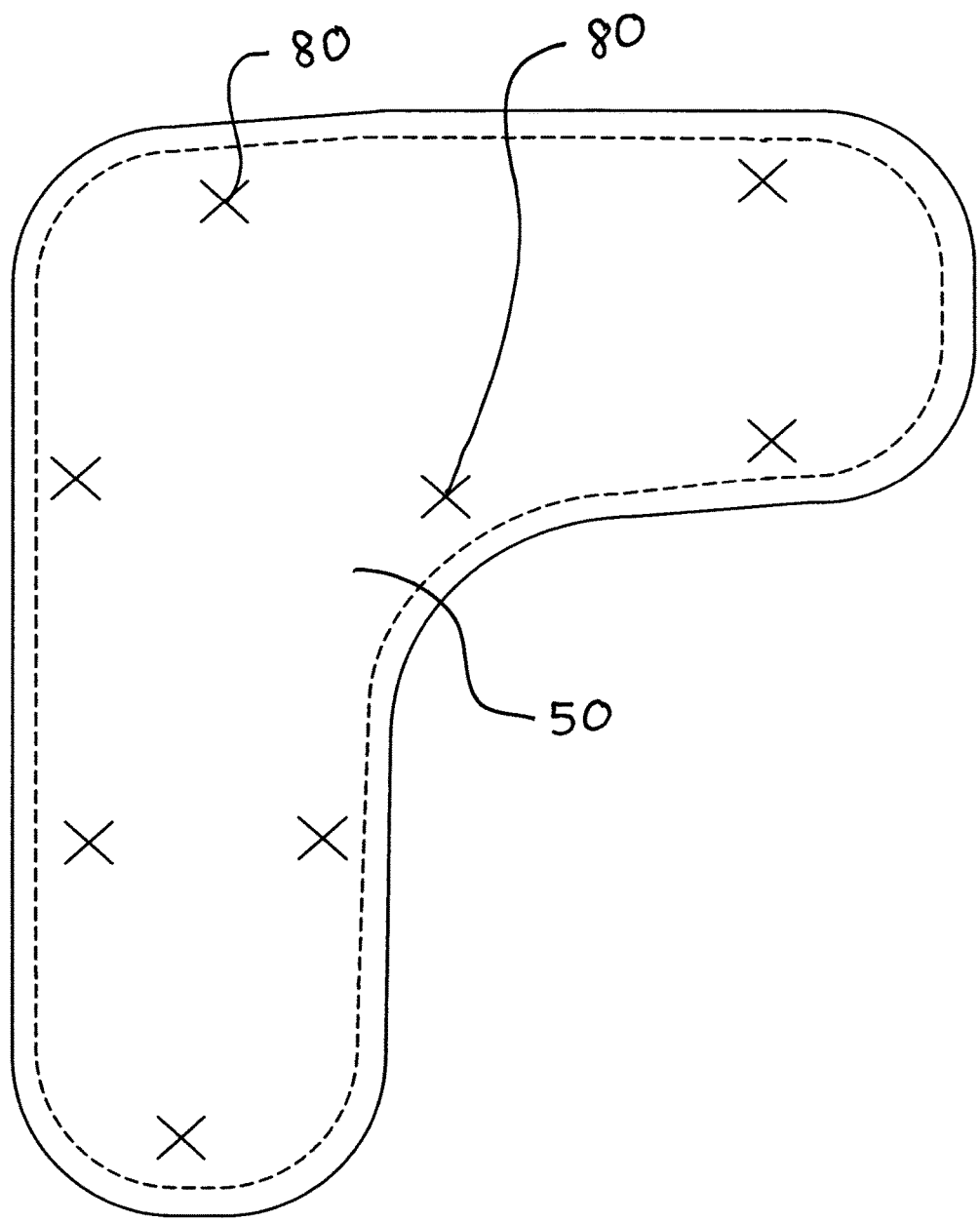
FIG. 5 is an embodiment of a lower insert.

FIG. 5 illustrates a lower insert 50 or torso insert 50 with its own attachment elements or attachment means 80 to removably attach to the attachment means 80 of the inside 70.

Figure 6:
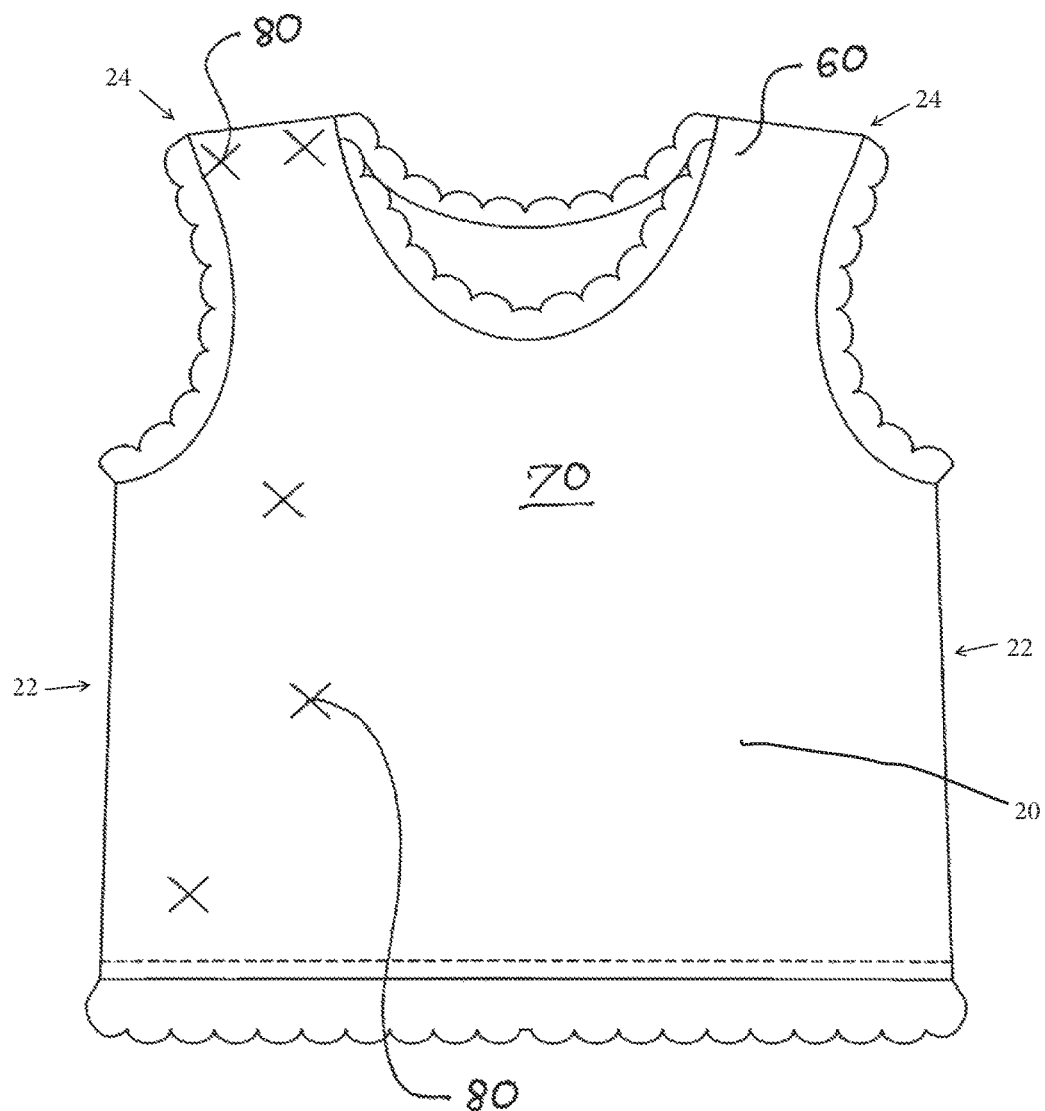
FIG. 6 is an embodiment of an inside front view of a main garment with means of attachment.

FIG. 6 illustrates an embodiment of the inside 70 front of the main garment 60. The attachment means 80 are shown on the inside 70 of main garment 60.

Figure 7:
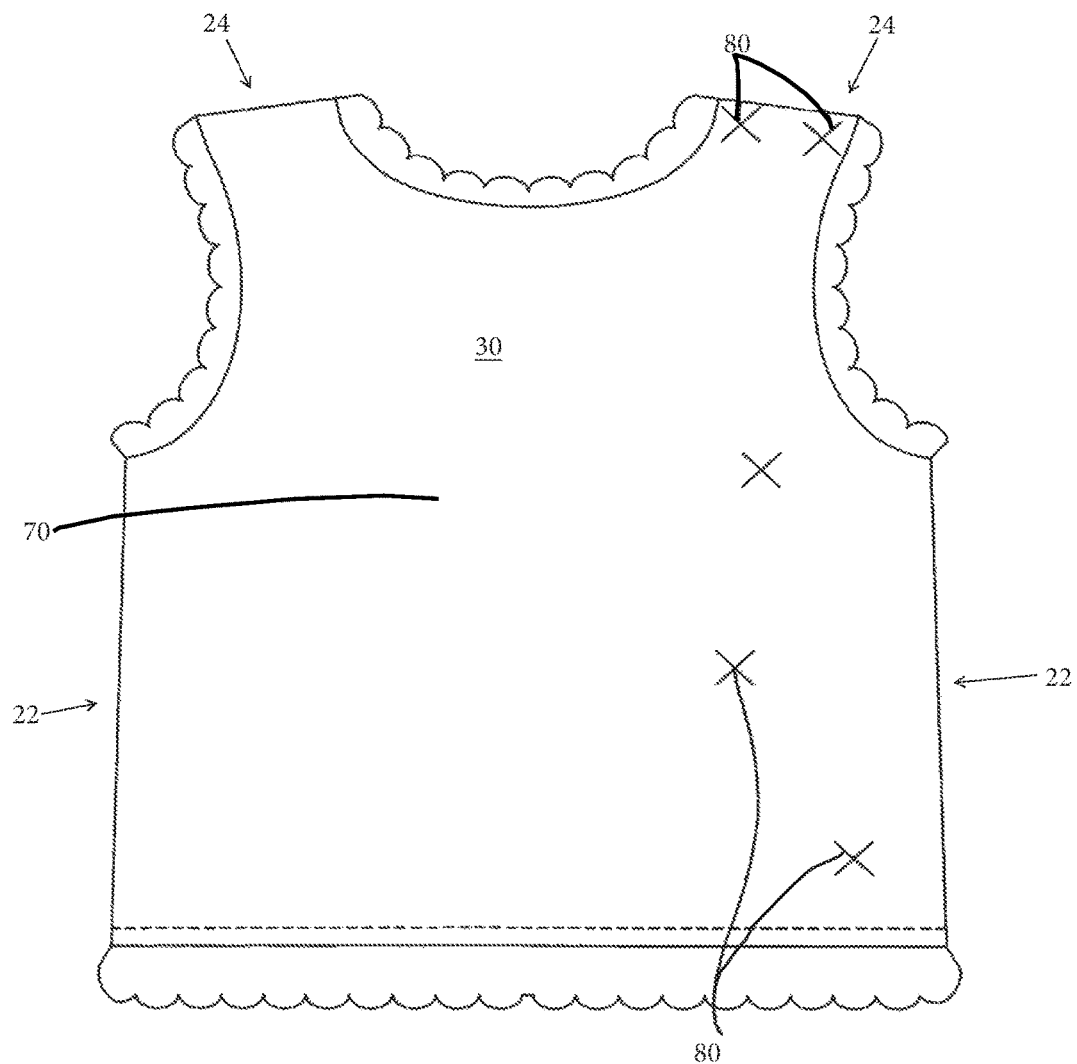
FIG. 7 is an embodiment of an inside rear view of a main garment with means of attachment.

FIG. 7 illustrates the inside 70 rear of the main garment 60 with attachment means 80 disposed thereon.

Figure 8A:
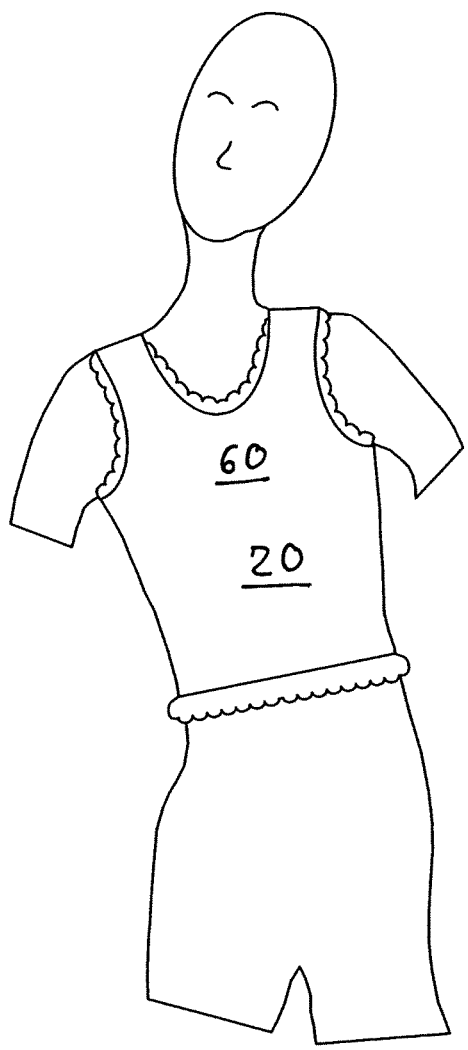
FIG. 8A illustrates a front view of the present invention being worn on a person.

FIG. 8A is a front view of the main garment 60 being worn.

Figure 8B:
FIG. 8B illustrates a rear view of the present invention being worn on a person.

FIG. 8B is a rear view of the main garment 60 being worn.

It should be understood, of course, that the foregoing relates to exemplary embodiments of the invention and that modifications may be made without departing from the spirit and scope of the invention as set forth in the following claims.

I claim:

1. An undergarment to compensate for contours of an asymmetric body shape of a scoliosis patient, said undergarment comprising:
a main garment adapted to be worn on the torso, said main garment having a front portion, a back portion, opposite side portions, and opposite shoulder portions at an upper region of said main garment, said main garment having respective inside surfaces at each of said front portion, said back portion, said opposite side portions, and said opposite shoulder portions;
a plurality of garment attachment elements in spaced arrangement along said inside surfaces of said main garment at each of said opposite side portions, at each of said front portion and said back portion, and at each of said opposite shoulder portions;
a shoulder insert comprising a shoulder insert attachment element configured for releasable engagement with any one of said garment attachment elements at either of said opposite shoulder portions, wherein said shoulder insert is configured for removable attachment to said main garment at said inside surface at either of said shoulder portions to selectively conceal contours of the asymmetric body shape proximate said shoulder portions to provide a less asymmetric outward appearance of the patient;
a torso insert adapted to extend along at least a portion of either of said opposite side portions or at least a portion of one of said front portion and said back portion; and
a torso insert attachment element at said torso insert and configured for releasable engagement with any of respective ones of said garment attachment elements at said either of said opposite side portions and said at least one of said front portion and said back portion;
wherein said torso insert is configured for removable attachment to said main garment along said inside surfaces of either of said side portions and at least one of said front portion and said back portion to selectively conceal contours of the asymmetric body shape proximate said side portions, said front portion, and said back portion to provide a less asymmetric outward appearance of the patient.

2. The undergarment of claim 1, wherein said torso insert is generally L-shaped, said torso insert comprising:
a first torso insert portion and a second torso insert portion angled relative to said first torso insert portion, wherein said torso insert attachment element comprises a first torso insert attachment element disposed along said first torso insert portion and configured for removable attachment to any of said garment attachment elements at either of said opposite side portions; and
a second torso insert attachment element disposed along said second torso insert portion and configured for removable attachment to any of said garment attachment elements at said at least one of said front portion and said back portion.

3. The undergarment of claim 1, wherein said shoulder insert and said torso insert each comprise padding material.

4. The undergarment of claim 3, wherein said shoulder insert and said torso insert are expandable.

5. The undergarment of claim 1, wherein said garment attachment elements comprise portions of hook-and-loop fasteners and each of said shoulder insert attachment element and said torso insert attachment element comprises corresponding portions of hook-and-loop fasteners.

6. The undergarment of claim 1, wherein said garment attachment elements comprise adhesive material.

7. The undergarment of claim 1, wherein each of said shoulder insert attachment element and said torso insert attachment element comprises adhesive material.

8. The undergarment of claim 1, wherein each of said shoulder insert attachment element and said torso insert attachment element comprises snaps.

9. An undergarment to compensate for contours of an asymmetric body shape of a scoliosis patient, said undergarment comprising:
a main garment adapted to be worn on the torso, said main garment having a front portion, a back portion, opposite side portions, and opposite shoulder portions at an upper region of said main garment, said main garment having respective inside surfaces at each of said front portion, said back portion, said opposite side portions, and said opposite shoulder portions;
a plurality of garment attachment elements in spaced arrangement along said inside surfaces of said main garment at each of said opposite side portions, at each of said front portion and said back portion, and at each of said opposite shoulder portions;

a padded shoulder insert comprising a shoulder insert attachment element configured for releasable engagement with any one of said garment attachment elements at either of said opposite shoulder portions, wherein said shoulder insert is configured for removable attachment to said main garment at said inside surface at either of said shoulder portions;

a plurality of padded torso inserts adapted to extend along said back portion or said front portion and configured for removable attachment to a respective plurality of said garment attachment elements at said main garment along said inside surface of each of said back portion and said front portion; and a torso insert attachment element at said torso insert and configured for releasable engagement with respective ones of said garment attachment elements at said back portion and said front portion;

wherein each of said padded shoulder inserts is freely removable and repositionable at any of said plurality of garment attachment elements at either of said shoulder portions to selectively conceal contours of the asymmetric body shape proximate said shoulder portions to provide a less asymmetric outward appearance of the patient, and wherein each of said torso inserts is freely removable and repositionable at any of said plurality of garment attachment elements at said front portion and at said back portion to selectively conceal contours of the asymmetric body shape proximate said front portion and said back portion to provide a less asymmetric outward appearance of the patient.

10. The undergarment of claim 9, wherein a first portion of each of said plurality of padded torso inserts is adapted to extend along said back portion, and a second portion of said padded torso inserts is angled relative to said first portion and adapted to extend along one of said opposite side portions, wherein said torso insert attachment element comprises a first torso insert attachment element disposed along said first portion of said torso insert and a second torso insert attachment element disposed along said second portion of said torso insert.

11. The undergarment of claim 10, wherein said torso insert is generally L-shaped.

12. The undergarment of claim 9, wherein said shoulder insert and said torso insert are expandable.

13. The undergarment of claim 9, wherein said garment attachment elements comprise portions of hook-and-loop fasteners and each of said shoulder insert attachment element and said torso insert attachment element comprises corresponding portions of hook-and-loop fasteners.

14. The undergarment of claim 9, wherein said garment attachment elements comprise adhesive material.

15. The undergarment of claim 9, wherein each of said shoulder insert attachment element and said torso insert attachment element comprise adhesive material.

16. The undergarment of claim 9, wherein each of said shoulder insert attachment element and said torso insert attachment element comprises snaps.

17. An undergarment to compensate for contours of an asymmetric body shape of a scoliosis patient, said undergarment comprising:

a main garment adapted to be worn on the torso, said main garment having a front portion, a back portion, opposite side portions, and opposite shoulder portions at an upper region of said main garment, said main garment having respective inside surfaces at each of said front portion, said back portion, said opposite side portions, and said opposite shoulder portions;

a plurality of garment attachment elements in spaced arrangement along said inside surfaces of said main garment at each of said opposite side portions, at each of said front portion and said back portion, and at each of said opposite shoulder portions;

a plurality of padded torso inserts, each of said plurality of padded torso inserts having a first torso insert portion adapted to extend along at least one of said front portion and said back portion, and a second torso insert portion angled relative to said first torso insert portion and adapted to extend along either of said opposite side portions;

a torso insert attachment element at said first torso insert portion configured for releasable engagement with any of said garment attachment elements at either of said opposite side portions; and a torso insert attachment element at said second torso insert portion configured for releasable engagement with any of said garment attachment elements at said at least one of said front portion and said back portion;

wherein said padded torso insert is configured for removable attachment to said main garment along said inside surfaces of either of said opposite side portions and at least one of said front portion and said back portion to selectively conceal contours of the asymmetric body shape proximate either of said side portions and at least one of said front portion and said back portion to provide a less asymmetric outward appearance of the patient.

18. The undergarment of claim 17, further comprising a padded shoulder insert having a shoulder insert attachment element configured for releasable engagement with any of said garment attachment elements at either of said opposite shoulder portions, wherein said shoulder insert is configured for removable attachment to said main garment at said inside surface at either of said shoulder portions to selectively conceal contours of the asymmetric body shape proximate either of said shoulder portions to provide a less asymmetric outward appearance of the patient, and wherein said torso insert is generally L-shaped.

19. The undergarment of claim 17, further comprising a plurality of said padded torso inserts adapted to extend along either of said opposite side portions of said garment and configured for removable attachment to a respective plurality of said garment attachment elements at said main garment along said inside surface of either of said opposite side portions, wherein said plurality of said padded torso inserts selectively conceal contours of the asymmetric body shape proximate either of said opposite side portions to provide a less asymmetric outward appearance of the patient.

* * * * *